(12) United States Patent
Saidi

(10) Patent No.: US 12,133,794 B2
(45) Date of Patent: Nov. 5, 2024

(54) NASAL IMPLANT INTRODUCED THROUGH A NON-SURGICAL INJECTION TECHNIQUE

(71) Applicant: Spirox, Inc., Menlo Park, CA (US)

(72) Inventor: Iyad S. Saidi, Arlington, VA (US)

(73) Assignee: Stryker Corporation, Portage, MI (US)

( * ) Notice: Subject to any disclaimer, the term of this patent is extended or adjusted under 35 U.S.C. 154(b) by 999 days.

(21) Appl. No.: 16/793,925

(22) Filed: Feb. 18, 2020

(65) Prior Publication Data

US 2020/0253726 A1 Aug. 13, 2020

Related U.S. Application Data

(60) Continuation of application No. 14/331,805, filed on Jul. 15, 2014, now Pat. No. 10,603,163, which is a continuation of application No. 13/348,105, filed on Jan. 11, 2012, now Pat. No. 8,784,488, which is a continuation of application No. 12/507,697, filed on Jul. 22, 2009, now Pat. No. 8,133,276, which is a division of application No. 11/898,768, filed on Sep. 14, 2007, now Pat. No. 7,780,730.

(60) Provisional application No. 60/846,736, filed on Sep. 25, 2006.

(51) Int. Cl.
*A61F 2/18* (2006.01)
*A61F 5/08* (2006.01)

(52) U.S. Cl.
CPC ............... *A61F 2/186* (2013.01); *A61F 2/18* (2013.01); *A61F 5/08* (2013.01)

(58) Field of Classification Search
CPC .. A61F 2/18; A61F 2/186; A61F 5/08; A61M 31/00; A61B 19/00
USPC ............. 623/10; 128/898; 606/185, 190–201
See application file for complete search history.

(56) References Cited

U.S. PATENT DOCUMENTS

| | | |
|---|---|---|
| 2,173,848 A | 9/1939 | Kraus |
| 3,395,709 A | 8/1968 | Rubin |
| 3,716,058 A | 2/1973 | Tanner, Jr. |
| 4,265,246 A | 5/1981 | Barry |
| 4,461,281 A | 7/1984 | Carson |

(Continued)

FOREIGN PATENT DOCUMENTS

| | | |
|---|---|---|
| EP | 1216013 B1 | 6/2006 |
| EP | 1857078 A | 11/2007 |

(Continued)

OTHER PUBLICATIONS

Friedman et al.; A simplified technique for airway correction at the nasal valve area; Otolaryngol Head Neck Surg; 131 (4); pp. 519-524; Oct. 2004.

(Continued)

*Primary Examiner* — Yashita Sharma
(74) *Attorney, Agent, or Firm* — McDonnell Boehnen Hulbert & Berghoff LLP

(57) ABSTRACT

A method for non-surgically treating an internal nasal valve of a patient comprising, injecting a working device into the internal nasal valve of the patient, wherein the injected working device in the nasal tissue causes an alteration of an internal or external nasal valve. A device introduced by injection into the nose, allowing for structural support or filling of defects in the nose, and causing a change in external shape of the nose. The device and inserts and implants described also have use in cosmetic applications relating to the facial tissue.

20 Claims, 16 Drawing Sheets

(56) References Cited

U.S. PATENT DOCUMENTS

| | | |
|---|---|---|
| 4,645,491 A | 2/1987 | Evans |
| 4,938,234 A | 7/1990 | Capriotti |
| 5,030,232 A * | 7/1991 | Pham .................. A61F 2/0059 623/10 |
| 5,131,382 A | 7/1992 | Meyer |
| 5,163,952 A | 11/1992 | Froix |
| 5,261,916 A | 11/1993 | Engelson |
| 5,286,254 A | 2/1994 | Shapland et al. |
| 5,342,348 A | 8/1994 | Kaplan |
| 5,356,431 A | 10/1994 | Pierce |
| 5,358,522 A | 10/1994 | Montgomery et al. |
| 5,411,550 A | 5/1995 | Herweck et al. |
| 5,419,760 A | 5/1995 | Narcisco |
| 5,464,450 A | 11/1995 | Buscemi et al. |
| 5,500,013 A | 3/1996 | Buscemi et al. |
| 5,531,744 A | 7/1996 | Nardella et al. |
| 5,533,440 A | 7/1996 | Sher |
| 5,545,208 A | 8/1996 | Wolff et al. |
| 5,551,954 A | 9/1996 | Buscemi et al. |
| 5,591,227 A | 1/1997 | Dinh et al. |
| 5,637,113 A | 6/1997 | Tartaglia et al. |
| 5,649,977 A | 7/1997 | Campbell |
| 5,679,400 A | 10/1997 | Tuch |
| 5,683,448 A | 11/1997 | Cragg |
| 5,730,744 A | 3/1998 | Justin et al. |
| 5,735,811 A | 4/1998 | Brisken |
| 5,749,893 A | 5/1998 | Vidal et al. |
| 5,766,237 A | 6/1998 | Cragg |
| 5,769,883 A | 6/1998 | Buscemi et al. |
| 5,785,647 A | 7/1998 | Tompkins et al. |
| 5,837,008 A | 11/1998 | Berg et al. |
| 5,843,172 A | 12/1998 | Yan |
| 5,891,108 A | 4/1999 | Leone et al. |
| 5,893,840 A | 4/1999 | Hull et al. |
| 5,897,523 A | 4/1999 | Wright et al. |
| 5,951,586 A | 9/1999 | Berg et al. |
| 5,972,027 A | 10/1999 | Johnson |
| 5,980,551 A | 11/1999 | Summers et al. |
| 5,980,564 A | 11/1999 | Stinson |
| 5,980,566 A | 11/1999 | Alt et al. |
| 6,010,054 A | 1/2000 | Johnson et al. |
| 6,063,101 A | 5/2000 | Jacobsen et al. |
| 6,071,305 A | 6/2000 | Brown et al. |
| 6,099,561 A | 8/2000 | Alt |
| 6,106,541 A | 8/2000 | Herbis |
| 6,165,210 A | 12/2000 | Lau et al. |
| 6,183,433 B1 | 2/2001 | Bays |
| 6,238,411 B1 | 5/2001 | Thorner |
| 6,241,747 B1 | 6/2001 | Ruff |
| 6,241,762 B1 | 6/2001 | Shanley |
| 6,250,307 B1 | 6/2001 | Conrad et al. |
| 6,268,405 B1 | 7/2001 | Conrad et al. |
| 6,290,673 B1 | 9/2001 | Shanley |
| 6,293,967 B1 | 9/2001 | Shanley |
| 6,322,590 B1 | 11/2001 | Sillers et al. |
| 6,390,096 B1 | 5/2002 | Conrad et al. |
| 6,401,717 B1 | 6/2002 | Conrad et al. |
| 6,415,796 B1 | 7/2002 | Conrad et al. |
| 6,431,174 B1 | 8/2002 | Knudson et al. |
| 6,450,169 B1 | 9/2002 | Conrad et al. |
| 6,454,803 B1 | 9/2002 | Romo |
| 6,516,806 B2 | 2/2003 | Knudson et al. |
| 6,656,195 B2 | 12/2003 | Peters et al. |
| 6,878,165 B2 | 4/2005 | Makino |
| 6,899,105 B2 | 5/2005 | Krueger et al. |
| 6,978,781 B1 | 12/2005 | Jordan |
| 6,982,359 B1 | 1/2006 | Beaudry |
| 7,055,523 B1 | 6/2006 | Brown |
| 7,114,495 B2 | 10/2006 | Lockwood |
| D536,792 S | 2/2007 | Krueger et al. |
| 7,213,599 B2 | 5/2007 | Conrad et al. |
| 7,237,554 B2 | 7/2007 | Conrad et al. |
| 7,322,356 B2 | 1/2008 | Critzer et al. |
| 7,322,993 B2 | 1/2008 | Metzger et al. |
| 7,337,781 B2 | 3/2008 | Vassallo |
| 7,381,222 B2 | 6/2008 | Pflueger et al. |
| 7,396,232 B2 | 7/2008 | Fromovich et al. |
| 7,419,497 B2 | 9/2008 | Muni et al. |
| 7,563,267 B2 | 7/2009 | Goldfarb et al. |
| 7,666,203 B2 | 2/2010 | Chanduszko et al. |
| 7,762,940 B2 | 7/2010 | Henderson et al. |
| 7,780,730 B2 | 8/2010 | Saidi |
| 7,992,566 B2 | 8/2011 | Pflueger et al. |
| 8,104,478 B2 | 1/2012 | Pflueger et al. |
| 8,133,276 B2 | 3/2012 | Saidi |
| 8,409,250 B2 | 4/2013 | Schmieding et al. |
| 8,784,488 B2 | 7/2014 | Saidi |
| 2002/0019670 A1 | 2/2002 | Crawley et al. |
| 2002/0173848 A1 | 11/2002 | Sachs |
| 2003/0028076 A1 | 2/2003 | Kuyava et al. |
| 2003/0149447 A1 | 8/2003 | Morency et al. |
| 2003/0199970 A1 | 10/2003 | Shanley |
| 2004/0098098 A1 | 5/2004 | McGuckin et al. |
| 2005/0004417 A1 | 1/2005 | Nelson et al. |
| 2005/0142162 A1 | 6/2005 | Hunter et al. |
| 2005/0154412 A1 | 7/2005 | Krueger et al. |
| 2006/0085027 A1 | 4/2006 | Santin et al. |
| 2006/0147492 A1 | 7/2006 | Hunter et al. |
| 2006/0184224 A1 | 8/2006 | Angel |
| 2006/0185680 A1 | 8/2006 | Bhat et al. |
| 2006/0241650 A1 | 10/2006 | Weber et al. |
| 2006/0276817 A1 | 12/2006 | Vassallo et al. |
| 2007/0173848 A1 | 7/2007 | Lennox et al. |
| 2007/0219575 A1 | 9/2007 | Mejia |
| 2007/0250118 A1 | 10/2007 | Masini |
| 2007/0277831 A1 | 12/2007 | Luhrs |
| 2007/0293946 A1 | 12/2007 | Gonzales et al. |
| 2008/0021495 A1 | 1/2008 | Lee et al. |
| 2008/0027480 A1 | 1/2008 | Van Der Burg et al. |
| 2008/0066794 A1 | 3/2008 | Durfee |
| 2008/0077240 A1 | 3/2008 | Saidi |
| 2008/0097335 A1 | 4/2008 | Trogden et al. |
| 2008/0167628 A1 | 7/2008 | Li et al. |
| 2008/0208265 A1 | 8/2008 | Frazier et al. |
| 2008/0234818 A1 | 9/2008 | Kang et al. |
| 2008/0312688 A1 | 12/2008 | Nawrocki et al. |
| 2009/0024133 A1 | 1/2009 | Keady et al. |
| 2009/0024227 A1 | 1/2009 | Lesh |
| 2009/0099577 A1 | 4/2009 | Gonzales |
| 2009/0198216 A1 | 8/2009 | Muni et al. |
| 2009/0318875 A1 | 12/2009 | Friedman |
| 2010/0174138 A1 | 7/2010 | Chang et al. |
| 2010/0280611 A1 | 11/2010 | Saidi |
| 2011/0251634 A1 | 10/2011 | Gonzales et al. |
| 2014/0243975 A1 | 8/2014 | Saidi et al. |

FOREIGN PATENT DOCUMENTS

| | | |
|---|---|---|
| EP | 1475056 B1 | 10/2010 |
| EP | 1940320 B1 | 12/2010 |
| WO | 0076493 A1 | 12/2000 |
| WO | 0101957 | 1/2001 |
| WO | 0119301 A1 | 3/2001 |
| WO | 2002076354 A1 | 10/2002 |
| WO | 03015664 | 2/2003 |
| WO | 2003041612 A2 | 5/2003 |
| WO | 2006093533 A1 | 9/2006 |
| WO | 2006101610 A2 | 9/2006 |
| WO | 2006107957 A1 | 10/2006 |
| WO | 2007134215 A2 | 11/2007 |
| WO | 2008042058 A1 | 4/2008 |
| WO | 2009036290 A1 | 3/2009 |

OTHER PUBLICATIONS

Kalan et al.; Treatment of external nasal valve (alar rim) collapse with an alar strut; Journal of Laryngology and Otology; 115(10); pp. 788-791; Oct. 2001.

Karen et al.; The use of percutaneous sutures for graft fixation in rhinoplasty; Archives Facial Plastic Surgery; 5(2); pp. 193-196; Mar.-Apr. 2003.

(56) References Cited

OTHER PUBLICATIONS

Lambert et al.; A new method for arterial drug delivery via removable stent (abstract); JACC; 21(2); p. 483A; Abstract No. 834-2; Feb. 1993.
Millman; Alar Batten grafting for management of collapsed nasal valve; Laryngoscope; 112(3); pp. 574-579; Mar. 2002.
Rhee et al.; Nasal valve surgery improves disease-specific quality of life; Laryngoscope; 115(3); pp. 437-440; Mar. 2005.
Westreich et al.; Defining nasal cartilage elasticity: Biomechanical testing of the tripod theory based on a cantilevered model; Arch Facial Plast Surg; 9(4); pp. 264-270; Jul./Aug. 2007.
Cole; Biophysics of nasal air flow: A review; American Journal of Rhinology; 14(4); pp. 245-249; Jul./Aug. 2000.
Cole; The four components of the nasal valve; American Journal of Rhinology; 17(2); pp. 107-100; Mar./Apr. 2003.
Fanous et al.; Collapsed nasal-valve widening by composite grafting to the nasal floor; Journal of Otolaryngology; 25 (5); pp. 313-316; Oct. 1996.
Friedman et al.; Nasal Valve Suspension: An Approved, Simplified Technique for Nasal Valve Collapse; Laryngoscope; 113(2); pp. 381-385; Jan. 2003.
Rosenthal et al.; U.S. Appl. No. 14/836,841 entitled "Nasal implants and systems and method of use," filed Aug. 26, 2015.
Parylene Engineering; Why use parylene; retrieved from the internet (http://www.paryleneengineering.com/why_use_parylene.htm); 3 pages; on Oct. 2, 2017.

\* cited by examiner

NASAL IMPLANT INTRODUCED THROUGH A NON-SURGICAL INJECTION TECHNIQUE

CROSS REFERENCE TO RELATED APPLICATIONS

This application is a continuation of U.S. application Ser. No. 13/348,105, filed Jan. 11, 2012, which claims the benefit of priority under 35 U.S.C. § 120 of U.S. application Ser. No. 12/507,697, filed Jul. 22, 2009, now U.S. Pat. No. 8,133,276, which is a divisional of U.S. application Ser. No. 11/898,768, filed Sep. 14, 2007, now U.S. Pat. No. 7,780,730, which claims the benefit of priority under 35 U.S.C. § 119(e) of U.S. Application No. 60/846,736, filed Sep. 25, 2006. The entire contents of each are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

STATEMENT AS TO FEDERALLY SPONSORED RESEARCH

This invention has been created without the sponsorship or funding of any federally sponsored research or development program.

FIELD

The invention relates to methods, implants, and devices for non-surgically supporting the nasal valve, and achieving cosmetic changes to the shape of the nose (e.g., rhinoplasty). The device is introduced through an injectable method into the nasal tissue, and by specially designed suture.

BACKGROUND

The information provided below is not admitted to be prior art to the present invention, but is provided solely to assist the understanding of the reader.

The internal nasal valve is the narrowest point in the nasal airway and is the point that often limits inspiration flow. A large percentage of inspiratory resistance is attributable to internal nasal valve function or malfunction. Collapse of one or both internal nasal valves is a common cause of nasal airway obstruction. Narrowness of the nasal valve may lead to difficulty in respiration and snoring as well as other breathing related disorders such as sleep apnea. Internal nasal valve collapse can be a consequence of previous surgery, trauma, aging, or primary weakness of the upper or lower lateral cartilage and is often symptomatic and debilitating.

A description of the nasal valve and its functions are more fully described in Cole, "The Four Components of the Nasal Valve", American Journal of Rhinology, Vol. 17, No. 2, pp. 107-110 (2003). See also, Cole, "Biophysics of Nasal Air Flow: A Review", American Journal of Rhinology, Vol. 14, No. 4, pp. 245-249 (2000).

Surgery to strengthen the nasal valve has been shown to significantly improve quality of life for treated patients. Rhee, et al., "Nasal Valve Surgery Improves Disease—Specific Quality of Life", Laryngoscope, Vol. 115, pp. 437-440 (2005). The most common procedure for treating nasal valve collapse is the so-called alar batten grafting. In batten grafting, a patient's cartilage is harvested from any one of a number of locations such as the nasal septum or the ear. The cartilage is sculpted to an appropriate size and shaped and beveled on the edges for improved cosmetics. The batten graft is placed in the desired location of the nasal passage through either an external or endonasal approach. A pocket is formed overlying the cartilages of the nose with the pocket sized to receive the batten graft. Placement of the batten graft is shown in FIG. 4 (page 577) of Millman, et al., "Alar Batten Grafting for Management of the Collapsed Nasal Valve", Laryngoscope, Vol. 112, pp. 574-579 (2002). Other nasal valve surgeries are described in Kalan, et al., "Treatment of External Nasal Valve (Alar Rim) Collapse with an Alar Strut", Journal of Laryngology and Otology, Vol. 115, pages 788-791 (2001); Karen, et al., "The Use of Percutaneous Sutures for Graft Fixation in Rhinoplasty", Archives Facial Plastic Surgery, Vol. 5, pp. 193-196 (2003) and Fanous, "Collapsed Nasal-Valve Widening by Composite Grafting to the Nasal Floor", Journal of Otolaryngology, Vol. 25, No. 5, pp. 313-316 (1996).

The harvesting of a portion of the patient's natural cartilage is an additional procedure and requires sculpting or other modification of the graft prior to use.

Accordingly, surgically implanted synthetic nasal dilators, and non-surgical external dilators and cones have been suggested. An example of a surgically implanted dilator is found in U.S. Pat. No. 6,106,541 to Hurbis dated Aug. 22, 2000. In the '541 patent, the nasal dilator has a V-shape with an apex placed over the bridge of the nose to support the nasal tissue at the area of the internal valve. Other examples include U.S. Pat. No. 6,322,590 to Sillers et al., dated Nov. 27, 2001. However, use of such devices require an open surgical technique for insertion.

External (non-implanted) nasal dilators which are placed temporarily, and are removed by the patient are also available. Such external devices are possibly placed on the outside surface of the nose such as the "Breathe Right" strips, U.S. Pat. No. 5,533,440, or U.S. Pat. No. 7,114,495 by Lockwood. Other devices may be placed in the nasal cavity (but not implanted in the nose), such as U.S. Pat. No. 7,055,523 given to Brown, and U.S. Pat. No. 6,978,781 given to Jordan. However, such devices can be uncomfortable, unsightly, and require the patient to remove and replace the device on a periodic basis.

Therefore, there is an urgent need for identifying methods and systems for repairing nasal valves and related nasal structures, including the repairing of the internal nasal valve collapse, which would eliminate the need for invasive surgical techniques. And thus eliminating risks and costs of general anesthesia and operating room expenses, and shorten recovery periods. It is also desirable to identify methods and systems that are implanted within the nose, eliminating the need for disposable external devices.

Unlike previous implant methods known and described, the implant of this invention is inserted by means of an injection technique, and does not require surgical incisions. It is inserted percutaneously or transmucosally, usually under local anesthetic only. The implant may have different shapes and/or physical properties than previous implants described. This allows for it to be inserted by means of a non surgical technique, and the position may be adjusted initially after placement. One aspect of the invention would permit the implant to be adjusted after implantation.

Unlike previous nasal strips and dilators, the current invention provides a device and means whereby the device(s) is embedded within the tissue of the nose. It is designed to be permanent or long lasting. It is not visible externally, and does not require the replacement or the adjustment by the patient and/or the physician.

SUMMARY OF THE DISCLOSURE

Objects of the present invention include providing a method and system for treating internal nasal valve collapse. According to the present invention, this is achieved by non-surgical or minimally invasive treatment. Treatment of the internal nasal valve includes injecting a working implant into the tissue of the patient, affecting the internal nasal valve of the patient. The injection of the implant of this invention into the tissue surrounding internal nasal valve, according to the invention, causes an alteration or a change in the internal nasal valve angle.

In certain embodiments, the increase in internal nasal valve angle is affected by the working device which causes an increase in the structural strength of the tissue surrounding the nasal valve, thus preventing the tissue from collapsing during inspiration.

In another embodiment, the working device is injected into more lateral structures of the nose which causes adjustment of the position of the lateral aspect of the lateral nasal cartilage whereby affecting the external nasal valve.

In another embodiment, the working device is injected into more lateral structures of the nose, strengthening the lateral nasal cartilage, supporting the external nasal valve, and preventing collapse during inspiration.

In another embodiment, the working device is injected into more lateral structures of the nose, strengthening the attachments of lateral nasal cartilage to the bone adjacent to the piriform aperture, and supporting the external nasal valve, and preventing collapse during inspiration.

In another embodiment, the treatment method includes inserting an implant adjacent to lower lateral cartilage, the nasal dorsum, the paramedian tissue of the nasal dorsum, or the collumella to change the external shape of the nose.

In another embodiment, the implant is cylindrical in shape, though other shapes have also been described and fall within the scope of the present invention. The size is selected such that the implant can fit in the core of a needle (similar to a hypodermic needle). It is introduced into the nasal tissue by inserting the needle into the desired location. The implant is then maintained in that position by application of gentle pressure on the implant by an advancement shaft as the needle is withdrawn.

In another embodiment the implant has variable physical properties, depending on the particular application. Implants may have a rigid or flexible shape or configuration. The insert may be moldable such that the shape is changed and maintained just before or after implantation, or later modified as desired by the patient or as needed to obtain the results desired. Furthermore, implants can have shape-memory, with a tendency to return to its preset shape when deflected.

In another embodiment of the invention, the invention relates to an injection device for introducing the implant, which comprises of an introduction needle containing the implant.

In another embodiment the implant may have sutures attached at either or both ends, and a separate guiding needle attached to at least one end of one of the sutures. This needle may be passed along the desired path of the implant. The attached sutures can then be used to guide the implantation of the implant, and to adjust position in the tissue immediately after implantation. These sutures may then be trimmed as needed.

The treatment method, according to embodiments of the invention, may be used to treat nasal snoring, sleep apnea, and/or internal nasal valve collapse.

In another embodiment, a system for non-surgically treating the nasal valves of a patient or changing the shape of the nose includes an introducing needle, an implant present within the needle, an advancement shaft, and a handle portion. In certain embodiments of the invention, there may be a stop element to possibly control the movement of the advancement shaft after the introduction needle containing the implant is placed in the desired location.

In another embodiment, the system includes a pre-loaded syringe with a working device. In one embodiment, the working device is comprising a solid or a semi-solid material, or a hollow or a non-hollow cylinder of material. In another embodiment, the working device is comprising a woven mesh of material, biodegradable material, or a combination thereof.

In certain embodiments, the nasal implant proposed is an implant introduced into the nose through an injection technique, either transmucosally from inside the nose, or transcutaneously, from outside the nose.

The implant of the present invention is intended for insertion into the nose tissue and serves to augment or modify the structure of the nose and the nasal or flow passages. The implant provides support of nasal valves in the nose and may serve to fill defects and/or supplement or modify the contour of the nose in the manner desired for the purpose.

The implant is introduced into a desired location within the nose or nasal passageway using an injection method. The implant is first incorporated into an injection device. The injection device may include a stop mechanism which serves to indicate when the implant is fully implanted.

The implant may be of any appropriate shape, including a cylindrical, an oval, or a rectangular and may include one or more tapered ends.

The implant of the present invention may be malleable, which would permit the shape of the implant to be adjusted before or after implantation. While not required, it may be preferred to use an implant made of a material which has shape memory properties. This property would permit the shape memory properties to be activated, or adjusted after implantation with the application of an external condition, such as temperature, magnetic field, or light.

In another embodiment of the invention, the implant may have spring like properties.

In another embodiment of the invention, the implant may be manufactured from a solid material, a composite of materials and may be a single material or may be a composite of one or more materials. The implant may be in the form of a rod or rod-like structure or may have a woven or braided structure. The implant may be woven or braided with several materials. In addition, the implant may be manufactured with biodegradable materials, including those with shape memory.

The implant may be introduced or injected through a transmucosal or transcutaneous route. The implant may be implanted within soft tissue of the nose in a location appropriate to provide the desired effect or result. When implanted into the soft tissue of the nose, the implant may serve to support the soft tissue relative to the underlying bone structure. Further, the implant may be used to augment the lower lateral cartilages of the nose. In another aspect of the invention the implant may be placed in the nose superior or inferior to the nasal cartage. Further it may be placed in a manner which will serve to augment the dorsum of the nose, or the collumella and may additionally be placed in a paramedian location in the nose.

In another embodiment, the implant along with the inserting device and may be altered to be used in other areas of the body such as, but not limited to, naso-labial folds, lips, and marrienette lines.

One embodiment of the invention is to provide a non-surgical approach for treating and eliminating these cosmetic conditions whether related to nasal valve problems or any other cosmetic related conditions.

The implant may be introduced into the desired location using a pull through technique, a guiding needle, or a combination of such techniques. The implant may be provided separately or with an injection device. Where desired the implant may incorporate a special pull through suture. The implant may additionally include a trailing suture. Where a pull through needle or trailing suture is used, both may be made or manufactured using materials which are dissolvable after the implant process is completed.

BRIEF DESCRIPTION OF THE DRAWINGS

In FIG. 14A the introduction needle containing the implant is first introduced through the nasal mucosa, and deep to the lower lateral cartilage. The introduction needle is then advanced into the desired location for the implant (FIG. 14B). The introduction needle is then withdrawn, as the implant is maintained in position by advancing the advancement shaft (FIG. 14C). After removal of the introduction needle, the implant is now present in the desired location (FIG. 14D). In certain situations, the implants shape may then be adjusted after implantation to assume the desired shape (FIG. 14E).

In FIG. 15A through 15C, the guiding needle is first introduced and passed to along the path through which the implant will be placed. The "pull through" suture is then advanced. The implant is then advanced, usually with the guide of an introduction needle system as shown in FIG. 15D. The introduction needle is removed while the advancement shaft is advanced to maintain the implant in the desired location (FIG. 15E). The pull through and trailing sutures may then be used to finely adjust the position of the implant after implantation (FIG. 15F). The sutures are then cut off at the skin or mucosal surface FIG. 15G).

DETAILED DESCRIPTION

Figure 1:
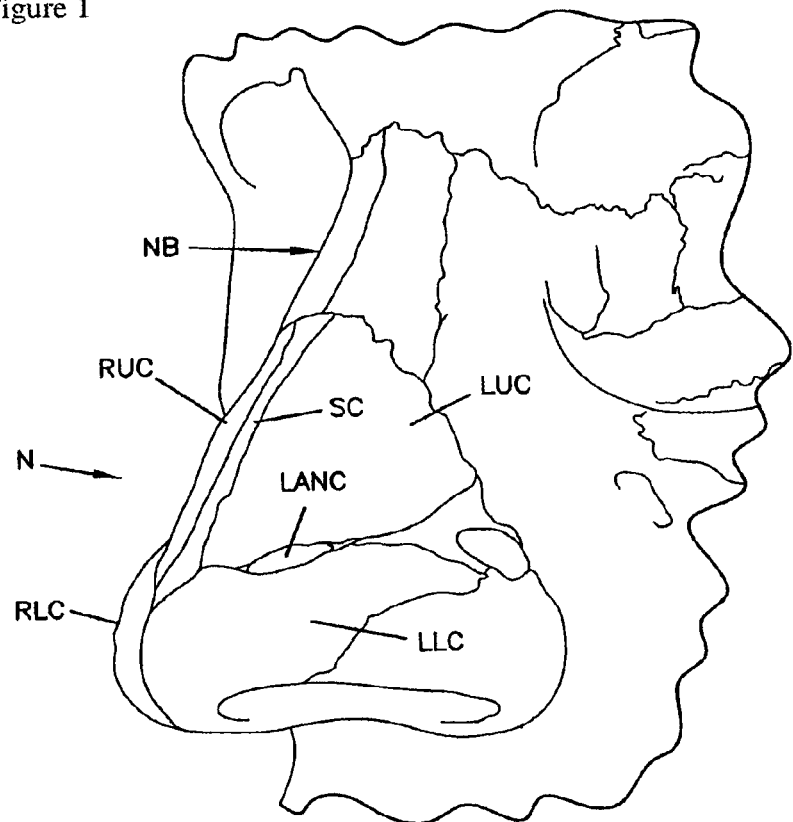
FIG. 1 is a perspective view of the front, top and left side of a patient's nose showing skeletal components and cartilages. Labeled are the Nose (N). Nasal bone (NB), Left upper cartilage (LUC), Right upper lateral cartilage (RUC), septal cartilage (SC), Right lower lateral cartilage (RLC), and Left lower lateral cartilage (LLC), and Left accessory nasal cartilage (LANC).

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing the subject components of the invention that are described in the publications, which components might be used in connection with the presently described invention.

The information provided below is not admitted to be prior art to the present invention, but is provided solely to assist the understanding of the reader.

The details of one or more embodiments of the invention are set forth in the accompanying drawings and the description below. Other features, objects, and advantages of the invention will be apparent from the description and drawings, and from the claims.

The structure of the lower two thirds of the nose is determined primarily by the nasal septal cartilage, and paired upper and lower lateral cartilages, covered by a soft tissue envelope [FIGS. 1-4]. Structural weakness of these cartilages, or their attachments may result in deleterious functional and cosmetic changes to the nose. The nasal valves may collapse contributing to a dynamic nasal obstruction. Internal and external nasal valves exist.

Figure 5:
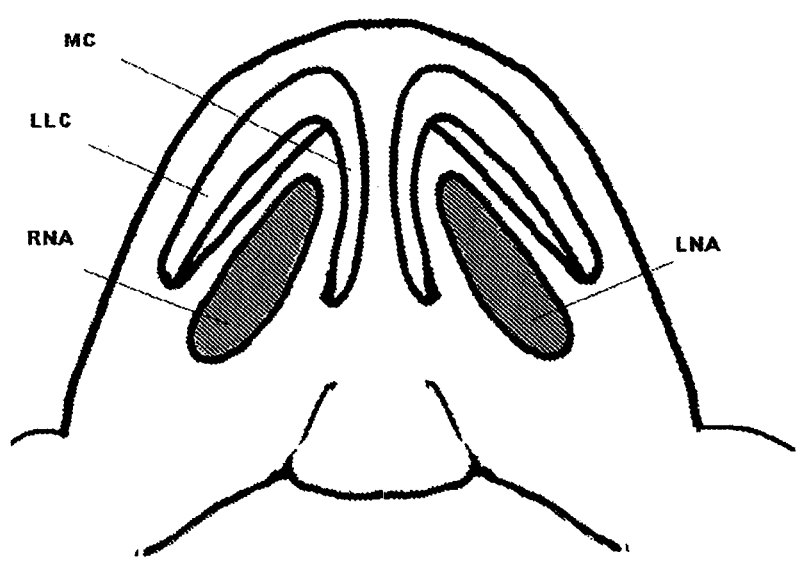
FIG. 5 is a bottom plan view of the nose showing the relation of the lower lateral cartilage (LLC) to the Medial cartilage (MC) and both their relationship to the nasal airway (NA). The Right nasal airway (RNA), and left nasal airway (LNA) are illustrated.
Figure 6:
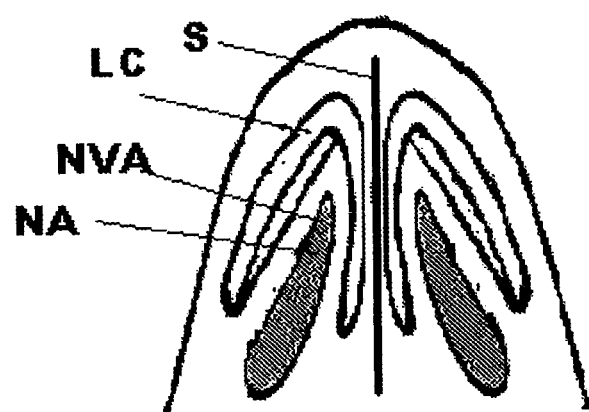
FIG. 6 is a cross sectional view of the nose. The Lateral cartilage (LC) refers to either the upper or lower lateral cartilage, depending on the area of collapse. The Nasal valve angle (NVA) is the angle created by the lateral cartilage and the septum (S). The lateral cartilage in this case is thinner, and weaker, and there is corresponding narrowing of the nasal airway (NA) due to collapse and narrowing of the nasal valve.

The internal nasal valves are formed by the angle of the septum and the lower edge of the upper lateral cartilage [FIG. 5]. During inspiration, air flow creates a negative pressure on the cartilage, resulting in a collapse of the nasal walls, as seen in FIG. 6. This leads to nasal obstruction. In some cases there may also be collapse of the nasal valve at rest, resulting in a constricted airway even at rest which is further exacerbated with inspiration.

The external valve is formed by the shape of the lower lateral cartilage, and the strength of the attachments of these lower lateral cartilages to the lateral anterior maxillary bone. Weakening of this lateral cartilage also leads to airway obstruction which is exacerbated with inspiration.

Nasal patency is critical to the airway, and nasal obstruction can contribute to snoring, sleep apnea, and disrupted sleep. The patency of a good nasal airway is also critical for the growing number of people using continuous positive airway pressure (CPAP) for sleep apnea.

Collapse and weakening of the nasal cartilage can also lead to external deformities and cosmetic changes to the nose. Loss of support and volume of the lower lateral cartilages, mid-nasal portion or the dorsum can lead to undesirable cosmetic changes. Relative tissue defects on the dorsum of the nose may lead to an irregular nasal profile. These cosmetic differences have traditionally been addressed by surgical rhinoplasty.

Common causes of nasal cartilage and nasal valve collapse today are prior surgery or trauma that weakens the cartilage, age, or congenital weakness of the nasal cartilage.

Current therapies to correct nasal valve collapse include several non-surgical and surgical devices and techniques. Non-surgical devices include external splints placed on the nasal surface which splay the lateral nasal walls outwardly, thus widening the nasal airway. External strips are such an external device (U.S. Pat. Nos. 5,533,440, 6,238,411, 6,982, 359, 7,114,495). Other devices previously proposed include cone shaped applicators placed into the nostril, or dilators having a variety of proposed shapes (U.S. Pat. Nos. 7,055, 523, 6,978,781).

Surgical therapies for repair of the valve collapse include insertion of spreader grafts (for internal valve collapse), batton grafts (for external valve collapse), or suspension sutures. These are placed through surgical incision techniques, or external rhinoplasty approach. The grafts are most commonly harvested from septal or auricular cartilage.

Implants (e.g., stents) made from alloplastic materials inserted surgically through an external approach have also been described (U.S. Pat. Nos. 6,106,541, 6,454,803, 6,322, 590, 2,173,848). These prevent the morbidity or limitations of homografts, but still require an incision surgical technique for placement.

Implants introduced through injection technique have been introduced into the palate and used for the treatment of snoring and sleep apnea (U.S. Pat. No. 7,077,144).

With reference to the figures provided herewith, in which identical elements are numbered identically throughout, a description of the preferred embodiment of the present invention will now be provided.

A. Anatomy

Figure 2:
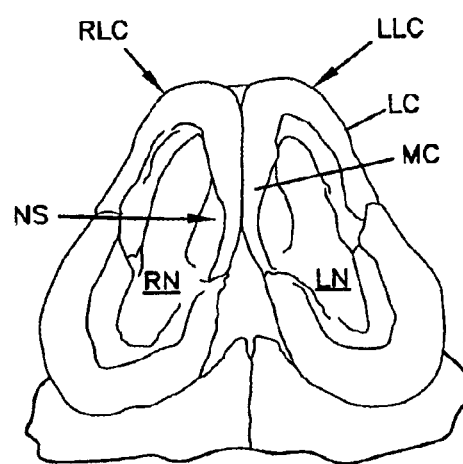
FIG. 2 is a bottom plan view of the components of FIG. 1. In addition to the labels above, the Medial Crus (MC) and Lateral Crus (LC) are labeled, which together comprise the lateral cartilage. The Right Nose (RN) and Left nose (LN) are also labeled.
Figure 3:
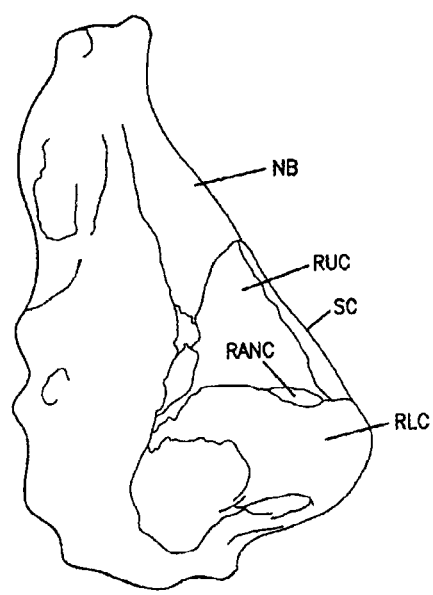
FIG. 3 is a right side elevation view of the components of FIG. 1. In this illustration, in addition to the labels above, the Right accessory nasal cartilage (RANC) is shown.
Figure 4:
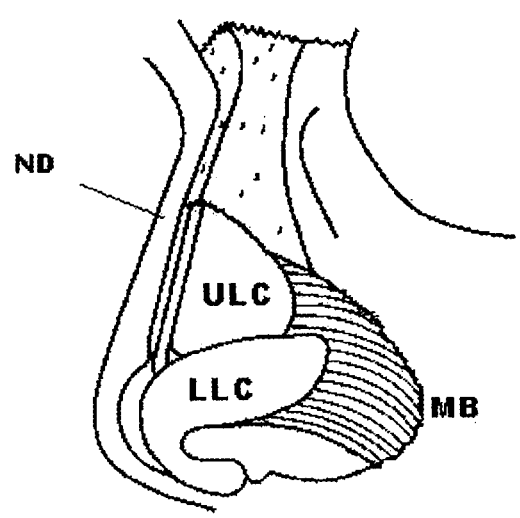
FIG. 4 is an oblique lateral view of the nasal structures. The nasal dorsum has both a bony and a cartilaginous component to give the nose the lateral profile. The upper lateral cartilage (ULC), and lower lateral cartilages (LLC) are labeled, and give the nose its structure. The Maxillary bone (MB) is the bone of the maxilla adjacent to the nose. The nasal shape and valve is also affected by the strength of the attachment of the lower lateral cartilage to the maxillary bone.

Before proceeding with a description of the apparatus and method of the present invention, a review of relevant anatomy will facilitate an understanding of the present invention. FIGS. 1-3 show in perspective, bottom plan and right side elevation, respectively, components of the nose with skeletal muscle, soft tissue (such as external skin or nasal mucosa) and blood vessels removed.

The nose N includes nasal bone NB at an upper end of the nose. The bottom of the nose N includes the lower cartilage also referred to as the major alar cartilage. There is both a right lower cartilage RLC and a left lower cartilage LLC, which are generally symmetrical in structure.

The lower cartilages RLC, LLC include an external component referred to as the lateral crus LC and an internal component referred to as the medial crus MC. The medial crus and septal nasal cartilage create a nasal septum NS divide the nose N into a left nostril LN and a right nostril RN.

Upper cartilages reside between the lower cartilages and the nasal bones NB. The upper cartilages include both a right upper cartilage RUC and a left upper cartilage LUC separated by a septal cartilage SC extending down the bridge of the nose N. The opposing edges of the lower cartilage LLC, RLC and upper cartilage LUC, RUC may move relative to one another. Disposed between the opposing edges is an accessory nasal cartilage (left and right) LANC, RANC.

When congested, during inhalation, airflow through the nostrils creates an inward pressure at the junction between the upper and lower cartilages. This pressure is expressed as a function of nasal resistance which is estimated as 10 centimeters of water per one liter per second. Cole, "The Four Components of the Nasal Valve", American Journal of Rhinology, pages 107-110 (2003).

In response to these forces, a weakened nasal valve may collapse inwardly as illustrated in FIG. 6. In FIG. 6, it will be appreciated that the inward deflection is exaggerated for ease of illustration. It will be noted with reference FIG. 5 that the narrow angle between the LLC and the MC illustrated in FIG. 6, and the relative weakness of the LLC contribute to the inward deflection and collapse of the airway.

B. Implant

1. The Implant:

The implant to be used in the present invention should be adapted for deployment in a nose. Thereto, the implant should be adapted for introduction into the nose of a patient, to be reliably positioned or installed within said nose and/or to be retained in said nose. The adaptation may be such that the form (or shape) of the implant is adapted or preformed to the anatomy of the nose for which it is intended. For example, the location in the nose and the required effect (e.g. bulking only or stiffening) may dictate that different shaped implants, or implants with different materials be used. The implant is self-holding when imbedded in the tissue.

Implants that can be used in the present invention include metallic implants, polymeric implants, biodegradable implants and covered or coated implants. They may be composed of a variety of metal compounds and/or polymeric materials, fabricated in innumerable designs, composed of degradable and/or nondegradable components, fully or partially covered with graft materials (such as the so called "covered stents") or "sleeves", and can be bare metal or drug-eluting.

The implants may be comprised of a metal or metal alloy such as stainless steel, spring tempered stainless steel, stainless steel alloys, gold, platinum, super elastic alloys, cobalt-chromium alloys and other cobalt-containing alloys ((including ELGILOY (Combined Metals of Chicago, Grove Village, Ill.), PHYNOX (Alloy Wire International, United Kingdom) and CONICHROME (Carpenter Technology Corporation, Wyomissing, Pa.)), titanium-containing alloys, platinum-tungsten alloys, nickel-containing alloys, nickel-titanium alloys (including nitinol), malleable metals (including tantalum); a composite material or a clad composite material and/or other functionally equivalent materials; and/or a polymeric (non-biodegradable or biodegradable) material. Representative examples of polymers that may be included in the implant construction include polyethylene, polypropylene, polyurethanes, polyesters, such as polyethylene terephthalate (e.g., DACRON or MYLAR (E. I. DuPont De Nemours and Company, Wilmington, Del.), polyamides, polyaramids (e.g., KEVLAR from E.I. DuPont De Nemours and Company), polyfluorocarbons such as poly(tetrafluoroethylene with and without copolymerized hexafluoropropylene) (available, e.g., under the trade name TEFLON (E. I. DuPont De Nemours and Company), silk, as well as the mixtures, blends and copolymers of these polymers. Stents also may be made with engineering plastics, such as thermotropic liquid crystal polymers (LCP), such as those formed from p,p'-dihydroxy-polynuclear-aromatics or dicarboxy-polynuclear-aromatics.

Further types of implants (e.g., stents) that can be used with the described therapeutic agents are described, e.g., in PCT Publication No. WO 01/01957 and U.S. Pat. Nos. 6,165,210; 6,099,561; 6,071,305; 6,063,101; 5,997,468; 5,980,551; 5,980,566; 5,972,027; 5,968,092; 5,951,586; 5,893,840; 5,891,108; 5,851,231; 5,843,172; 5,837,008; 5,766,237; 5,769,883; 5,735,811; 5,700,286; 5,683,448; 5,679,400; 5,665,115; 5,649,977; 5,637,113; 5,591,227; 5,551,954; 5,545,208; 5,500,013; 5,464,450; 5,419,760; 5,411,550; 5,342,348; 5,286,254; and 5,163,952. Removable drug-eluting stents are described, e.g., in Lambert, T. (1993) J. Am. Coll. Cardiol.: 21: 483A. Moreover, the stent may be adapted to release the desired agent at only the distal ends, or along the entire body of the stent.

In addition to using the more traditional stents, stents that are specifically designed for drug delivery can be used. Examples of these specialized drug delivery stents as well as traditional stents include those from Conor Medsystems (Palo Alto, Calif.) (e.g., U.S. Pat. Nos. 6,527,799; 6,293,967; 6,290,673; 6,241,762; U.S. Patent Application Publication Nos. 2003/0199970 and 2003/0167085; and PCT Publication No. WO 03/015664).

Other examples of stents that can be used in accordance with the invention include those from Boston Scientific Corporation, (e.g., the drug-eluting TAXUS EXPRESS[2] Paclitaxel-Eluting Coronary Stent System; over the wire stent stents such as the Express2 Coronary Stent System and NIR Elite OTW Stent System; rapid exchange stents such as the EXPRESS[2] Coronary Stent System and the NIR ELITE MONORAIL Stent System; and self-expanding stents such as the MAGIC WALLSTENT Stent System and RADIUS Self Expanding Stent); Medtronic, Inc. (Minneapolis, Minn.) (e.g., DRIVER ABT578-eluting stent, DRIVER ZIPPER MX Multi-Exchange Coronary Stent System and the DRIVER Over-the-Wire Coronary Stent System; the S7 ZIPPER MX Multi-Exchange Coronary Stent System; S7, S670, 5660, and BESTENT2 with Discrete Technology Over-the-Wire Coronary Stent System); Guidant Corporation (e.g., cobalt chromium stents such as the MULTI-LINK VISION Coronary Stent System; MULTI-LINK ZETA Coronary Stent System; MULTI-LINK PIXEL Coronary Stent System; MULTI-LINK ULTRA Coronary Stent System; and the MULTI-LINK FRONTIER); Johnson & Johnson/Cordis Corporation (e.g., CYPHER sirolimus-eluting Stent; PALMAZ-SCHATZ Balloon Expandable Stent; and S.M.A.R.T. Stents); Abbott Vascular (Redwood City, Calif.) (e.g., MATRIX LO Stent; TRIMAXX Stent; and DEX- AMET stent); Conor Medsystems (Menlo Park, Calif.) (e.g., MEDSTENT and COSTAR stent); AMG GmbH (Germany) (e.g. PICO Elite stent); Biosensors International (Singapore) (e.g., MATRIX stem, CHAMPION Stent (formerly the S-STENT), and CHALLENGE Stent); Biotronik (Switzerland) (e.g., MAGIC AMS stent); Clearstream Technologies (Ireland) (e.g., CLEARFLEX stent); Cook Inc. (Bloomington, Ind.) (e.g., V-FLEX PLUS stent, ZILVER PTX self-expanding vascular stent coating, LOGIX PTX stent (in development); Devax (e.g., AXXESS stem) (Irvine, Calif.); DISA Vascular (Pty) Ltd (South Africa) (e.g., CHROMOFLEX Stent, S-FLEX Stent, S-FLEX Micro Stent, and TAXOCHROME DES); Intek Technology (Baar, Switzerland) (e.g., APOLLO stent); Orbus Medical Technologies (Hoevelaken, The Netherlands) (e.g., GENOUS); Sorin Biomedica (Saluggia, Italy) (e.g., JANUS and CARBOSTENT); and stents from Bard/Angiomed GmbH Medizintechnik KG (Murray Hill, N.J.), and Blue Medical Supply & Equipment (Marietta, Ga.), Aachen Resonance GmbH (Germany); Eucatech AG (Germany), Eurocor GmbH (Bonn, Gemany), Prot, Goodman, Terumo (Japan), Translumina GmbH (Germany), MIV Therapeutics (Canada), Occam International B.V. (Eindhoven, The Netherlands), Sahajanand Medical Technologies PVT LTD. (India); AVI Biopharma/Medtronic/Interventional Technologies (Portland, Oreg.) (e.g., RESTEN NG-coated stent); and Jomed (e.g., FLEXMASTER drug-eluting stent) (Sweden). Other types of stents can be in US20060147492A1: Medical implants and anti-scarring agents. The entire content of US20060147492A1 is incorporated herein by reference.

Generally, the implants are inserted in a similar fashion regardless of the site or the disease being treated. Briefly, a preinsertion examination is conducted by direct visualization, possible endoscopy, and rarely diagnostic imaging. The areas of structural defects, volume defects, of dynamic collapse of the nose are noted. The implant size and material is selected to suit the particular application, where more than one implant material and size may be available.

Topical local anesthetic may be applied by a combination of topical anesthetic cream applied to the skin (e.g. 4% lidocaine cream available commercially) and/or topical anesthetic solution (e.g 4% lidocaine solution) applied on a cotton pledget in the nasal cavity. Local anesthetic may be infiltrated directly in the area where the implant will be placed, or also injected to perform regional blocks, such as an infraorbital nerve block.

The implant is then introduced through an injection technique as illustrated in this patent (for example, see FIGS. 14A-14E). The implant is introduced through the injection method into the desired location in the nasal tissues. The introducing needle is gradually withdrawn, while the implant is maintained in its desired position by means of the advancement shaft of the introduction device. Generally, the puncture site performed by the introduction needle is small, and does not require repair.

After insertion, the implant shape may be adjusted manually. In some situations a special condition is applied to allow for adjustment of the shape of the implant. For example, in the case of an implant with certain physical properties, heat may be applied by external application of a heating pad to the nose. This is transmitted through the tissue to the implant which raises its temperature. The shape of the implant is then adjusted to the desired shape, and the external heat source is removed. The implant then maintains this new shape as it is cools.

A post insertion examination, is performed to visually confirm that the desired structural and shape change to the nose has been achieved. Rarely, diagnostic imaging or endoscopy may also be used at this stage.

Implants are typically maneuvered into place directed by visual and tactile control. In certain aspects, the implant (e.g., stent) can further include a radio-opaque, echogenic material, or MM responsive material (e.g., MRI contrast agent) to aid in visualization of the device under ultrasound, fluoroscopy and/or magnetic resonance imaging. The radio-opaque or MM visible material may be in the form of one or more markers (e.g., bands of material that are disposed on either end of the implant).

As suitable implant materials, both organic and inorganic materials, as well as combinations thereof may be used. The material of the implant may be solid, (e.g. titanium, nitinol, or Gore-tex), braided or woven from a single material (such as titanium, or Polyethylene Terephthalate, or a combination of materials). The woven materials may have pores which allow ingrowth of tissue after implantation. It may be manufactured from biodegradable materials (e.g poly-L lactic, Poly-D lactic, and poly-L glycolic acid) which will gradually absorb after implantation. It may be malleable, allowing adjustment of the shape before, or after implantation.

Synthetic polymers provide for very suitable organic implant (e.g., stent) materials. Advantages of such polymers include the ability to tailor mechanical properties and degradation kinetics to suit various applications. Synthetic polymers are also attractive because they can be fabricated into various shapes. Numerous synthetic polymers can be used to prepare synthetic polymer-comprising stents useful in aspects of the invention. They may be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif.

Representative synthetic polymers include alkyl cellulose, cellulose esters, cellulose ethers, hydroxyalkyl celluloses, nitrocelluloses, polyalkylene glycols, polyalkylene oxides, polyalkylene terephthalates, polyalkylenes, polyamides, polyanhydrides, polycarbonates, polyesters, polyglycolides, polymers of acrylic and methacrylic esters, polyacrylamides, polyorthoesters, polyphe azenes, polysiloxanes, polyurethanes, polyvinyl ohols, polyvinyl esters, polyvinyl ethers, polyvinyl halides, polyvinylpyrrolidone, poly(ether ether ketone)s, silicone-based polymers and blends and copolymers of the above. The stent may comprise both oligomers and polymers of the above.

Specific examples of these broad classes of polymers include poly(methyl methacrylate), poly(ethyl methacrylate), poly(butyl methacrylate), poly(isobutyl methacrylate), poly(hexyl methacrylate), poly(isodecyl methacrylate), poly (lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), poly(vinyl acetate), poly(vinyl chloride), polystyrene, polyurethane, poly(lactic acid), poly(butyric acid), poly(valeric acid), poly[lactide-co-glycolide], poly(fumaric acid), poly(maleic acid), copolymers of poly (caprolactone) or poly (lactic acid) with polyethylene glycol and blends thereof.

The polymers used in implants (e.g., stents) may be non-biodegradable. Examples of preferred non-biodegradable polymers include ethylene vinyl acetate (EVA), poly (meth)acrylic acid, polyamides, silicone-based polymers and copolymers and mixtures thereof.

Polymers used in implants (e.g., stents) may also be biodegradable. The rate of degradation of the biodegradable stent is determined by factors such as configurational structure, copolymer ratio, crystallinity, molecular weight, morphology, stresses, amount of residual monomer, porosity and site of implantation. The skilled person will be able to choose the combination of factors and characteristics such that the rate of degradation is optimized.

Examples of preferred biodegradable polymers include synthetic polymers such as polyesters, polyanhydrides, poly (ortho)esters, polyurethanes, siloxane-based polyurethanes, poly(butyric acid), tyrosine-based polycarbonates, and natural polymers and polymers derived therefrom such as albumin, alginate, casein, chitin, ch[embedded image not shown]osan, collagen, dextran, elastin, proteoglycans, gelati[embedded image not shown] and other hydrophilic proteins, glutin, zein and other prolamines and hydrophobic proteins, starch and other polysaccharides including cellulose and derivatives thereof (e.g. methyl cellulose, ethyl cellulose, hydropropyl cellulose, hydroxy-propyl methyl cellulose, hydroxybutyl methyl cellulose, carboxymethyl cellulose, cellulose acetate, cellulose propionate, cellulose acetate butyrate, cellulose acetate phthalate, cellulose acetate succinate, hydroxypropylmethylcellulose phthalate, cellulose triacetate, cellulose sulphate), poly-1-lysine, polyethyenimine, poly(allyl amine), polyhyaluronic acids, and combinations, copolymers, mixtures and chemical derivatives thereof (substitutions, additions of chemical groups, for example, alkyl, alkylene, hydroxylations, oxidations, and other modifications routinely made by those skilled in the art). In general, these materials degrade either by enzymatic hydrolysis or exposure to water in vivo, by surface or bulk erosion. The foregoing materials may be used alone, as physical mixtures (blends), or as a copolymer.

Other polymers are polyesters, polyanhydrides, polystyrenes and blends thereof. The polyesters and polyanhydrides are advantageous due to their ease of degradation by hydrolysis of ester linkage, degradation products being resorbed through the metabolic pathways of the body in some cases and because of their potential to tailor the structure to alter degradation rates. The mechanical properties of the biodegradable material are preferably selected such that early degradation and concomitant loss of mechanical strength required for its functioning as a structure supporting implant is prevented.

Biodegradable polyesters are for instance poly(glycolic acid) (PGA), poly(lactic acid) (PLA), poly(glycolic-co-lactic acid) (PGLA), poly(dioxanone), poly(caprolactone) (PCL), poly(3-hydroxybutyrate) (PHB), poly(3-hydroxyvalerate) (PHV), poly(lactide-co-caprolactone) (PLCL), poly(valerolactone) (PVL), poly(tartronic acid), poly(β-malonic acid), poly(propylene fumarate) (PPF) (preferably photo cross-linkable), poly(ethylene glycol)/poly(lactic acid) (PELA) block copolymer, poly(L-lactic acid-e-caprolactone) copolymer, and poly(lactide)-poly(ethylene glycol) copolymers.

Biodegradable polyanhydrides are for instance poly[1,6-bis(carboxyphenoxy)hexane], poly(fumaric-co-sebacic) acid or P(FA:SA), and such polyanhydrides may be used in the form of copolymers with polyimides or poly(anhydrides-co-imides) such as poly-[trimellitylimidoglycine-co-bis(carboxyphenoxy)hexane], poly[pyromellitylimidoalanine-co-1,6-bis (carboph-enoxy)-hexane], poly[sebacic acid-co-1,6-bis(p-carboxyphenoxy)hexane] or P(SA:CPH) and poly [sebacic acid-co-1,3-bis(p-carboxyphenoxy)propane] or P(SA:CPP).

Other suitable stent materials are biocompatible materials that are accepted by the tissue surface. The broad term biocompatible includes also nontoxicity, noncarcinogenity, chemical inertness, and stability of the material in the living body. Exemplary biocompatible materials are titanium, alumina, zirconia, stainless steel, cobalt and alloys thereof and ceramic materials derived therefrom such as ZrO2 and/or Al2O3.

As examples of inorganic implants (e.g., stents) materials calcium phosphate matrices (CaP) and hydroxyapatite (HA) matrices may be used, wherein HA may optionally be combined with tricalcium phosphate to form such compounds as biphasic calcium phosphate (BCP). CaP, sintered hydroxyapatite and bioactive glasses or ceramics, such as 45S5 Bioglass® (US Biomaterials Corp, USA), and apatite- and wollastonite-containing glass-ceramic (glass-ceramic A-W) may also be used. Very suitable matrix materials are the combined materials such as osteoinductive hydroxyapatite/(HA/TCP) matrices, preferably BCP.

One form of the nasal implant described here is introduced through an injection device. The implant (A) is elongated in shape having a length L and side profile P [FIG. 13 a]. The side profile may be oval in shape, rectangular, or tapered at the ends [FIG. 13 (b, c, and d)]. Furthermore, it may be a hollow cylinder (FIG. 13 e), or made of a composite of materials, or a braid of wires. They are introduced into the nose non-surgically through an injection device. The injection route may include transcutaneous route, i.e. through the nasal skin, or transmucossally, through the internal mucosa of the nose. The intention of this device is that it be introduced under local anesthetic.

Figure 11:
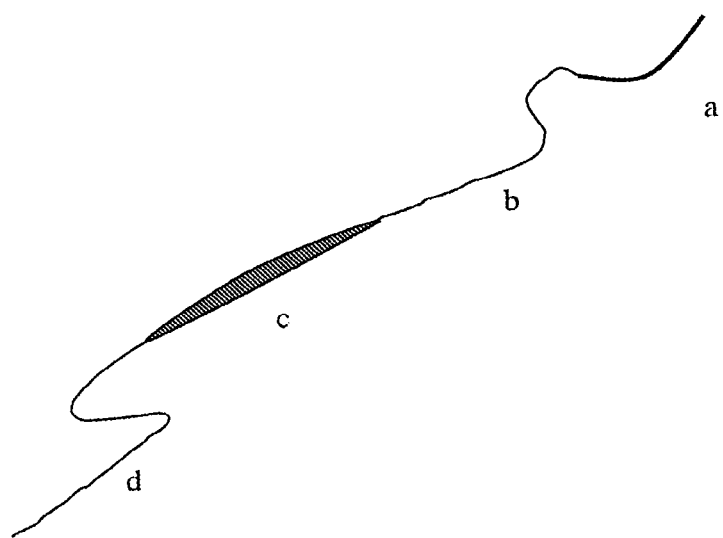
FIG. 11. The proposed modification to the nasal implant, where the implant, (c), has attached to it a guiding needle, (a), a "pull through" suture, (b), and a trailing suture, (d).
Figure 12A:
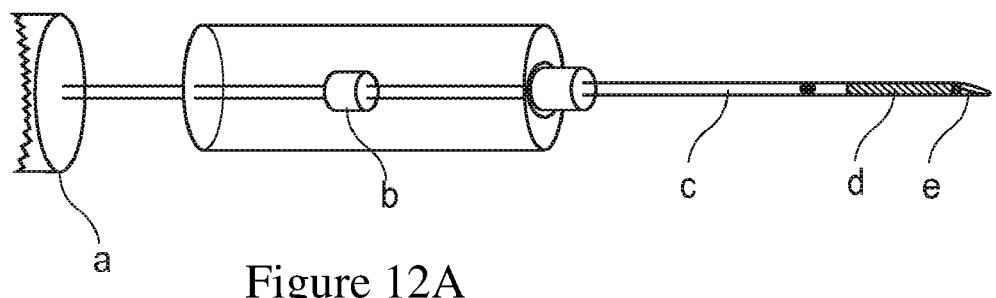
FIG. 12A. The introducing device composed of the implant (d) placed in an introducing needle (e). There is the advancement shaft (c) which is used to advance the implant (d), into the desired location. The stop (b) prevents the thumb control (a) and advancement shaft (c) from advancing after the implant is expressed from the introducing needle, and placed in the desired location in the tissue. In the attachments FIG. 12 B show an alternate arrangement in which the injector device (A) and the introduction needle and implant (B) are packaged separately, but can be attached through a locking attachment (f).
Figure 12B:
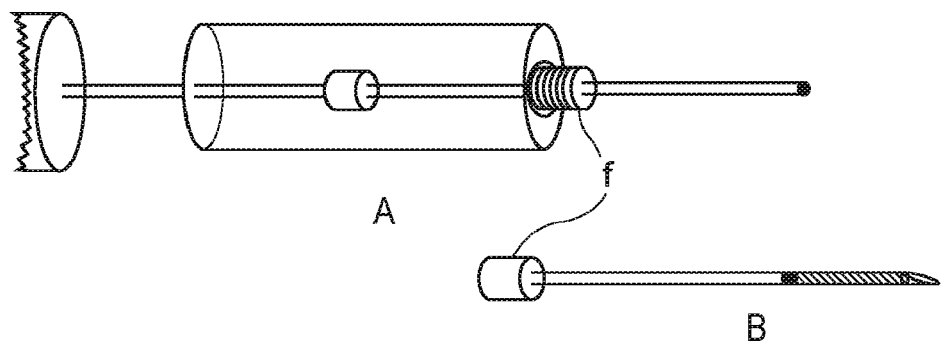

The nasal implant may also incorporate an introduction needle and suture, and/or a trailing suture (FIG. 11). This provides an alternative method for introduction of the implant. The guiding needle is introduced through the skin, or mucosa, and tracked along the desired path to the location chosen for the implant and then to a location where it exits the body, such as through the skin. This guiding needle is introduced and guided by the physicians fingers, or using standard medical instruments. This method for introduction of the implant which includes a "pull through" and trailing sutures is illustrated in FIGS. 15A-15G. After introduction of the "pull through" suture shown in FIGS. 15A-15G, the guiding needle may be cut off. The implant is then introduced with the injection device in FIGS. 12A-12B, with the guidance of the "pull through" suture, as illustrated in FIGS. 15A-15G. Alternatively, it may be introduced without an injection device, but simply by guiding it to the desired location by gently pulling on the "pull through" suture. The trailing suture can also be used to make adjustments to the position of the implant in situ. When the desired position is accomplished, the pull through suture, and the trailing sutures are cut. The suture can be made of absorbable material. The suture may have a diameter similar to the diameter of the implant, or be smaller or larger.

The injector device allows the introduction of the implant into the body through an injection technique. Shown in FIGS. 12A-12B, it incorporates the nasal implant (FIG. 14-d), an introducing needle (FIG. 14-e). The implants are introduced through an injection device either through the transcutaneous route or through the nasal mucosa. The implant is placed through a straight introducer device, or a specially curved introducer device, or may be malleable, to allow for special shaping of the needle prior to injection.

Figure 7:
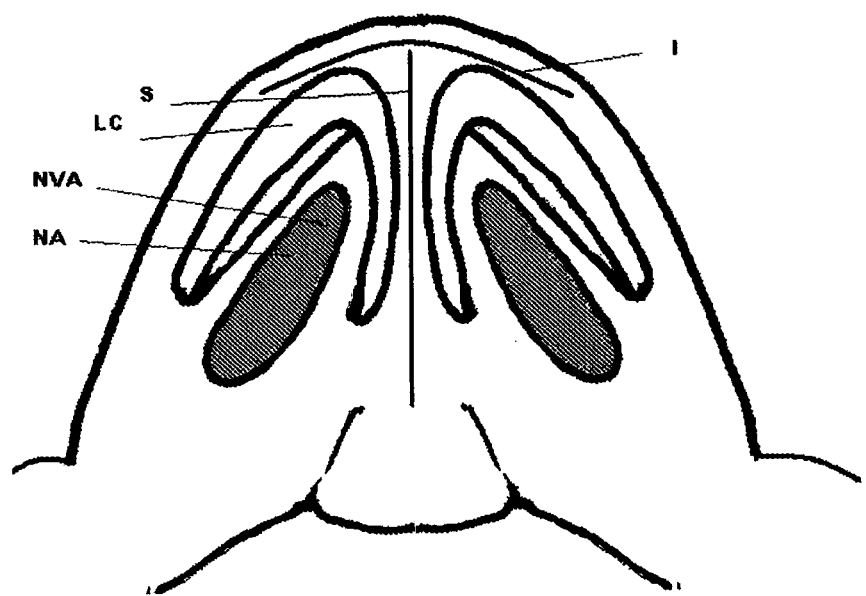
FIG. 7 is a cross sectional view of the nose after implantation of an implant (I). The Lateral cartilage (LC) is supported by the implant, (I). The Nasal valve angle (NVA) is thus supported from collapsing during inspiration, widening the nasal airway (NA). In this case the implant is implanted on the outer surface of the lateral cartilage and septum (S).

These implants may be placed adjacent to the upper lateral cartilage, below the nasal surface, as illustrated in FIG. 7. This will apply lateral force to the medial portion of the lateral nasal cartilage, stenting the internal nasal valves open. This is an alternative to the spreader grafts currently placed surgically.

Figure 8:
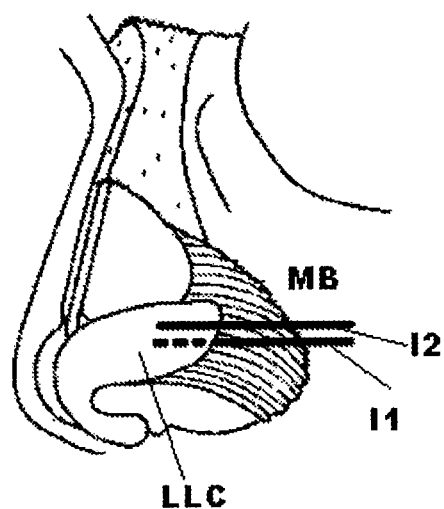
FIG. 8 is an oblique lateral view of the nasal structures after implantation of an two implants acting as a batten grafts. The lower lateral cartilages (LLC) and Maxillary bones (MB) are labeled. The implants (I1) and (I2) give support to the lateral edge of the lower lateral cartilage, and strengthen its attachments to the maxillary bone. In this illustration, the implant I1 is situated medial to the lower lateral cartilage, but overlying the maxillary bone, while implant I2 is placed lateral to the lower lateral cartilage, and also lateral to the maxillary bone.

The implants may be placed adjacent to the lateral edge of the lower lateral cartilages. The implants may extend to the bony process of the anterior maxillary bone as illustrated in FIG. 8. This will secure the lateral cartilage more securely to the maxillary bone, preventing lateral nasal collapse. These implants may be placed to secure the external valve in place of alar batten grafts that are now employed and are applied surgically. They may be inserted overlying or underlying the lateral surface of the lower lateral cartilage.

The implants may have a straight or curved shape. Alternately, they may have a malleable property, and can have the shape adjusted after implantation. They may also have shape memory properties (such as composed Nitinol) which allows for their shape to assume a predetermined shape after implantation. Use of inserts made of materials which have shape memory properties permit the implant to assume a preset shape after insertion. Alternately, certain conditions may be applied, such as application of heat, cold, light, or a magnetic field, that will allow the material to assume a desired fixed or modified shape after implantation. The necessary condition will depend on the intrinsic properties of the shape memory material chosen to produce the implant. The fixed shape of the implant may also be adjusted before or after insertion. The implant may be composed of biodegradable materials, with or without shape memory.

Figure 9:
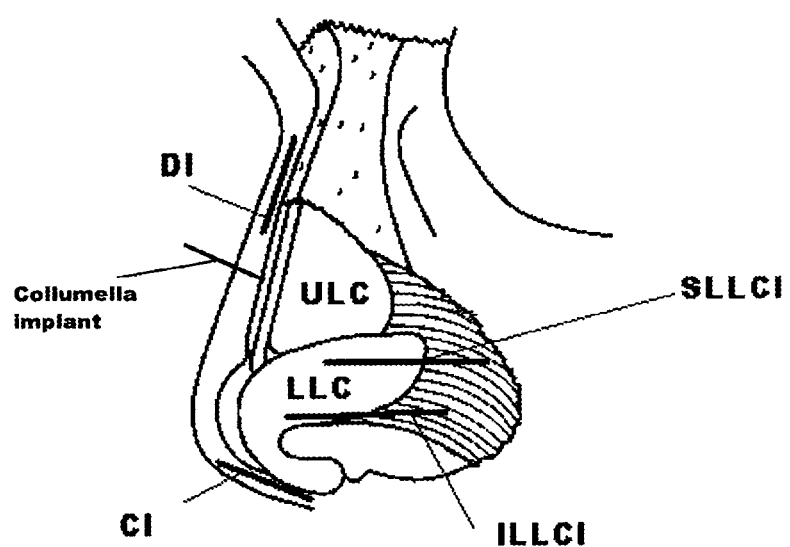
FIG. 9 is an oblique lateral view of the nasal structures after implantation of the proposed implants into other areas of the nose to achieve structural and cosmetic changes in the nose, not necessarily related to the nasal valve. Some of the implant locations proposed here and included for illustration purposes are: dorsal implants (DI), used to modify the dorsal profile of the nose; Inferior Lower Lateral Cartilage implant (ILLCI), which strengthens the lower lateral cartilage shape and form, thus also affecting the shape of the nose, and of the nasal tip; and Superior Lower Lateral Cartilage Implant (SLLCI) also used to modify the shape of the lower lateral cartilage, and the nasal form; and a Collumella Implant (CI) used to give support to the collumella.
Figure 10:
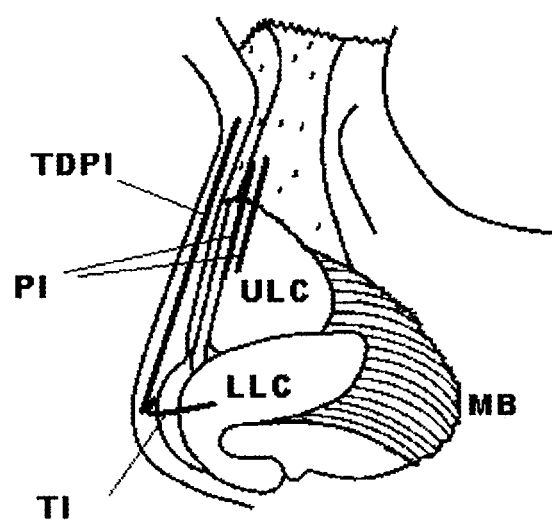
FIG. 10 is an oblique lateral view of the nasal structures after implantation of the proposed implants into further areas of the nose to achieve structural and cosmetic changes in the nose. Shown here is an implant that can be used as a Total Dorsal Profile Implant (TDPT), Paramedian Implants (PI), and Tip Implants (TI).

Another aspect of this invention provides for the use of the described injectable implants for cosmetic changes to the nose. The implants may be introduced transcutaneously or transmucosally to improve the structural strength of the nasal cartilages, or to fill defects in the nasal contours. Examples of proposed areas where the implants can be placed include locations adjacent to the lower lateral cartilage as lateral alar implants, in the mid nasal region, and the nasal dorsum, or the collumella, as illustrated in FIG. 9, and FIG. 10.

EXAMPLES

Three working examples of useful implants have been produced for insertion into the nose.

The first is a 1.4 cm long, 0.8 mm thick titanium rod that is incorporated in a 16 gauge injection needle. This is designed for use into the lateral nasal wall which supports the external valve. The implant is injected in a fashion similar to the technique illustrated in FIGS. 14A-14E. The currently preferred method of introduction is transmucosally (from inside the vestibule of the nose). The implant is placed between the lower lateral cartilage and the nasal mucosa, and extends over the maxillary bone. When placed, it appears similar to the implant I1 shown in FIG. 8. One implant is placed for each side of the nose, if bilateral valve collapse is present. After implantation, the shape of the implant can be adjusted by molding the shape of the titanium implant.

In another example, a 1.8 cm long and 1 mm thick rod manufactured from a 85:15 poly (L-lactide-co-glycolide) polymer has been produced. It is introduced using a J4 gauge needle. This polymer is bio-absorbable. It is inserted transcutaneously over the medial portion of the nose, similar to the one shown in FIG. 7. After implantation, the material has some structural strength, and by providing an upward force on the medial portion of the upper lateral curtilage, it supports the internal nasal valve, preventing its collapse. The shape of the implant can be adjusted after implantation by temporarily placing a heating pad at 64 degrees Celsius on the surface of the nose. This temperature is tolerated by the human nose for a brief period of time. The temperature is transmitted to the implant, and at such a temperature the polymer softens, and the implant shape can manually adjusted. The implant retains the new shape as it cools.

Figure 13A:
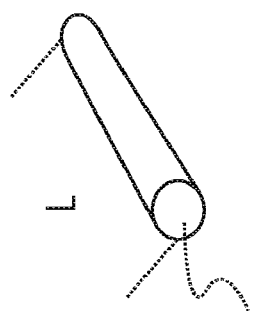
FIGS. 13A-13E. Representative shapes of the nasal implants. The implants in general is elongated in shape having a length L and side profile P as shown in [FIG. 13 *a*]. The side profile may be oval in shape (FIG. 13 *b*), rectangular or oblong (FIG. 13 *c*), or have tapered at the ends (FIG. 13 *d*). Furthermore, it may be a hollow cylinder, or made of two or more materials (FIG. 13 *e*).
Figure 13B:
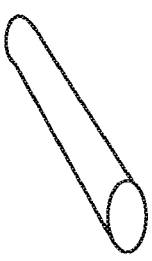
Figure 13C:
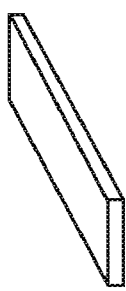
Figure 13D:
Figure 13E:
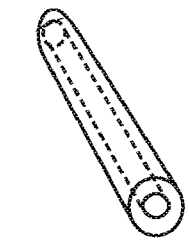
Figure 14A:
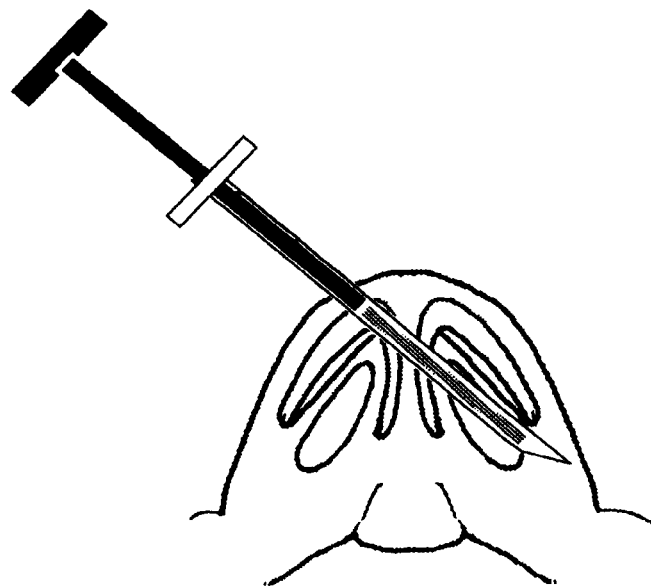
FIGS. 14A-14E. The standard introduction method of the implant, in this case implanted into the lateral nose, to support the external nasal valve.
Figure 14B:
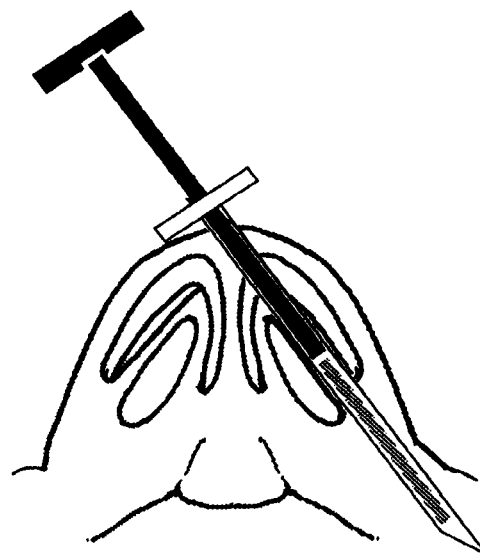
Figure 14C:
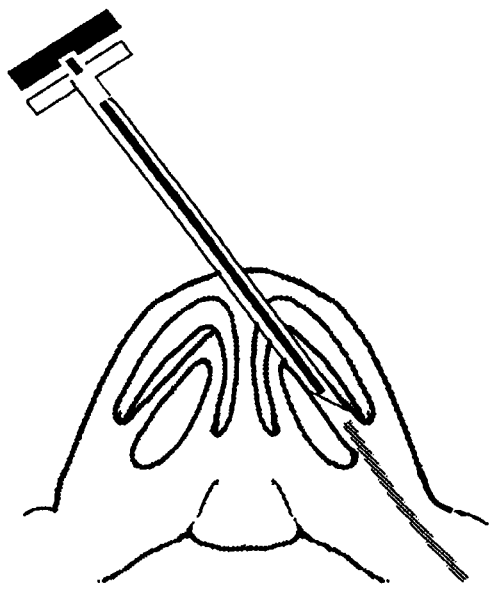
Figure 14D:
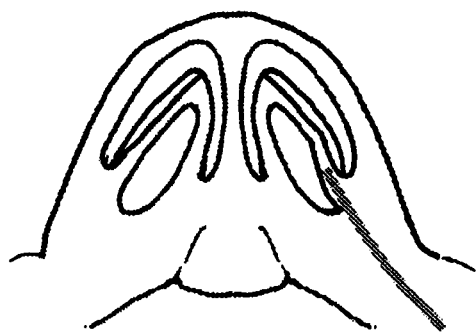
Figure 14E:
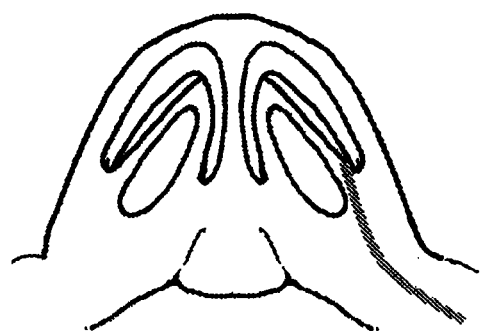
Figure 15A:
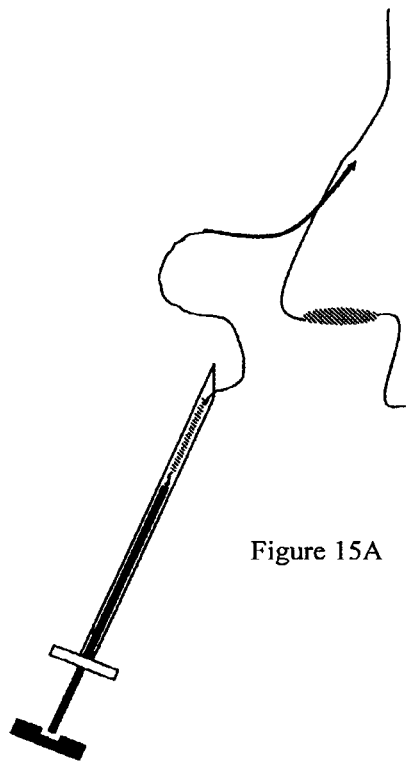
FIGS. 15A-15G. The introduction method using the additional introduction modification shown in FIG. 11.
Figure 15B:
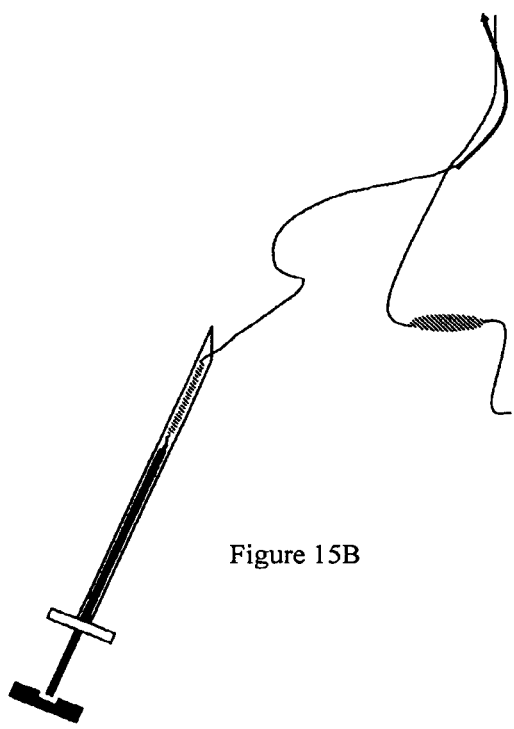
Figure 15C:
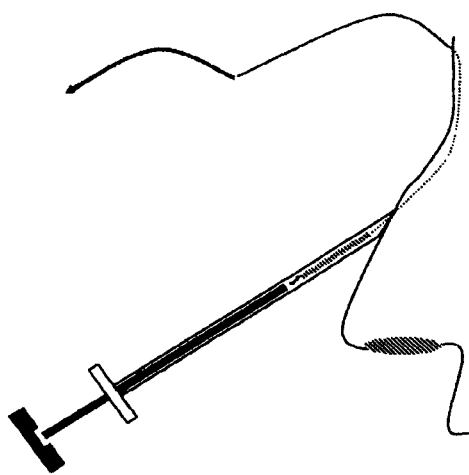
Figure 15D:
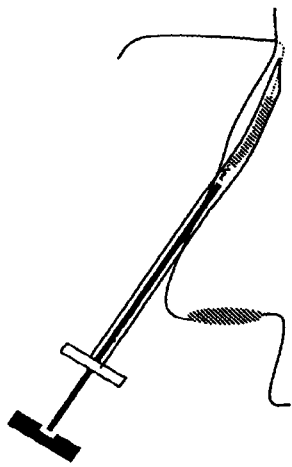
Figure 15E:
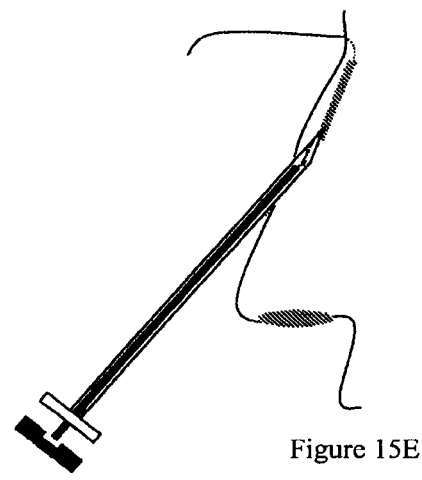
Figure 15F:
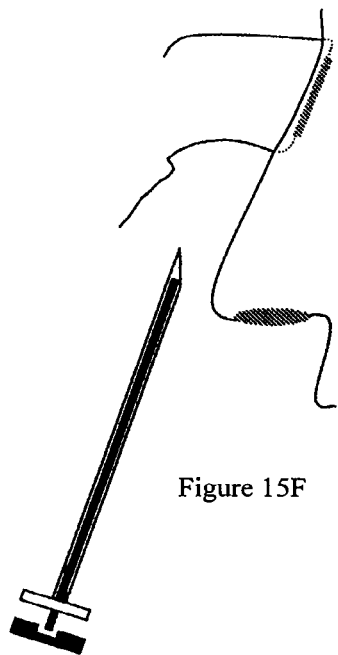
Figure 15G:

The third example used is a tapered rod with an oval shaped cross section similar to the implant shown in FIG. 13b. The implant dimensions may be trimmed prior to implantation depending on the particular size desired for the particular patient to be implanted. This implant is manufactured from a porous polyethylene. It is inert, non-absorbable, and has a porous structural surface which allows for fibrovascular tissue ingrowth. It is introduced through a 14 gauge needle, into the dorsum of the nose, filling in volume defects in the nose. This is similar to the DI implant shown FIG. 9.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method for implanting a nasal implant, comprising:
    transmucossally puncturing an introducing needle through an internal mucosa of a lateral nasal wall of a nose into nasal tissue of the nose at a puncture site within a nasal cavity of the nose, wherein the puncture site is at a vestibule of the nose, wherein puncturing the introducing needle through the nasal tissue at the puncture site is performed without forming an incision at the puncture site prior to puncturing the introducing needle through the nasal tissue at the puncture site, wherein the introducing needle comprises a hollow core that extends to a distalmost end of the introducing needle, wherein the distalmost end of the introducing needle is a beveled tip for puncturing the nasal tissue;
    after puncturing the introducing needle into the nasal tissue at the puncture site, advancing the introducing needle through the nasal tissue to a site of implantation in the nose;
    after advancing the introducing needle through the nasal tissue to the site of implantation, moving the nasal implant relative to the hollow core and out of the distalmost end of the introducing needle to deposit the nasal implant at the site of implantation in the nasal tissue of the nose; and
    removing the introducing needle from the nasal tissue via the puncture site.

2. The method of claim 1, wherein, when deposited at the site of implantation, the nasal implant extends from a lateral cartilage of the nose to a position over a maxillary bone of the nose.

3. The method of claim 1, wherein puncturing the introducing needle into the nasal tissue is performed while the nasal implant is in the hollow core of the introducing needle.

4. The method of claim 1, further comprising, responsive to moving the nasal implant relative to the hollow core, changing a shape of the nasal implant from a first shape to a second shape.

5. The method of claim 4, wherein the nasal implant is a spring structure.

6. The method of claim 4, wherein the nasal implant is expandable from the first shape to the second shape.

7. The method of claim 1, wherein the nasal implant comprises a coating.

8. The method of claim 1, wherein the nasal implant comprises a degradable component and a non-degradable component.

9. The method of claim 1, wherein the nasal implant is bioabsorbable.

10. The method of claim 1, further comprising applying a topical local anesthetic to the nose prior to puncturing an introducing needle into the nasal tissue.

11. The method of claim 1, wherein the introducing needle comprises an advancement shaft, and wherein moving the nasal implant relative to the hollow core of the introducing needle comprises moving the advancement shaft relative to the hollow core.

12. The method of claim 11, wherein the introducing needle further comprises a stop that prevents the advancement shaft from moving relative to the hollow core after the nasal implant is deposited at the site of implantation.

13. The method of claim 11, wherein the hollow core has a straight shape.

14. The method of claim 1, wherein, at the site of implantation, the nasal implant is entirely within the nasal tissue.

15. The method of claim 1, wherein puncturing the introducing needle into the nasal tissue and advancing the introducing needle are performed under direct visualization of the nose and the introducing needle.

16. The method of claim 1, wherein the nasal implant comprises a tapered rod.

17. The method of claim 1, wherein the nasal implant comprises a rod having a cross-sectional thickness of 1 millimeter.

18. The method of claim 1, further comprising supporting a nasal airway with the nasal implant to thereby prevent the nasal airway from collapsing during inspiration.

19. The method of claim 1, wherein a distal end of the nasal implant is delivered out the distalmost end of the introducing needle before a proximal end of the nasal implant.

20. The method of claim 7, further comprising eluting a drug from the nasal implant to the nasal tissue.

* * * * *